United States Patent [19]

Kuhlmann et al.

[11] Patent Number: 5,463,160
[45] Date of Patent: Oct. 31, 1995

[54] SKELETAL ISOMERIZATION OF N-PENTENES TO ISOPENTENE ON PRETREATED ZEOLITES

[75] Inventors: Erven J. Kuhlmann, Hopewell Junction; James R. Pascoe, Fishkill; Christopher J. Thom, Beacon, all of N.Y.

[73] Assignee: Texaco Inc., White Plains, N.Y.

[21] Appl. No.: 112,999

[22] Filed: Aug. 30, 1993

[51] Int. Cl.[6] ............................................. C07C 5/27
[52] U.S. Cl. ............................................... 585/671
[58] Field of Search ..................................... 585/671

[56] References Cited

U.S. PATENT DOCUMENTS

3,965,209  6/1976  Butter et al. .................. 585/454
5,157,194  10/1992  Rahmim et al. ................ 585/671
5,321,194  6/1994  Apelian et al. ................. 585/671

Primary Examiner—Anthony McFarlane
Assistant Examiner—E. D. Irzinski
Attorney, Agent, or Firm—George J. Darsa

[57] ABSTRACT

The selective conversion by skeletal isomerization over steam pretreated ferrierite zeolite-based catalysts having pore sizes of at least about 4.2 Angstroms and a pore structure characterized by intersecting 10-MR and 8-MR channels. The steam pretreated ferrierite zeolite-based catalysts have sufficient acidity to catalyze the skeletal isomerization of normal olefins. The catalysts can be used to produce isoolefins for reaction with alcohols in integrated processes to produce tertiary amyl methyl ethers such as TAME.

6 Claims, 4 Drawing Sheets

Isomerization of n-Pentenes
Effect of Steaming on Ferrierite Catalyst

SKELETAL ISOMERIZATION OF N-PENTENES TO ISOPENTENE ON PRETREATED ZEOLITES

BACKGROUND OF THE INVENTION

This invention relates to olefin isomerization. In one of its more specific aspects, this invention relates to selective isomerization of n-pentenes.

More particularly, the present invention relates to a process for the preparation of useful hydrocarbons by catalytic conversion of n-pentenes.

TAME (tertiary amyl methyl ether) is an effective octane booster as well as a source of oxygenates in gasoline that are effective in reducing CO and hydrocarbon emissions. It is made from 2-methylbutenes and methanol. The present sources of 2-methylbutene for TAME production are mainly from by-products of steam cracker, catalytic cracker and cokers. However, these supplies are limited. Other possible sources are by isomerization of n-pentenes taken from steam or catalytic crackers and by dehydrogenation of isopentane produced by isomerization of n-pentane.

Olefin isomerization processes can be directed towards either skeletal isomerization or double bond isomerization. Skeletal isomerization is concerned with reorientation of the molecular structure in respect to the formation or elimination of side chains. Double bond isomerization is concerned with relocation of the double bond between carbon atoms while maintaining the backbone of the carbon structure. Most isomerization processes give rise only to double bond isomerization.

It is frequently necessary to convert olefins into other olefins having a different skeletal arrangement. For example, normal butenes are converted into isobutene for polymerization, alkylation, disproportionation or for the production of MTBE. Similarly, normal pentenes must be converted to isoamylenes prior to dehydrogenation to isoprene.

While a number of catalytic materials possess some activity for such a conversion, not all possess sufficient selectivity to be economical. Because the feeds are generally the relatively reactive olefins, many catalysts cause undesirable side reactions such as oligomerization polymerization or cracking. Consequently, there is a continuing interest in the development of new or improved skeletal isomerization catalysts and processes for isomerizing alkenes to improve efficiencies and to give optimum results for various industrial requirements. A comprehensive review is provided by V. R. Choudhary in "Catalytic Isomerization of n-Butene to Isobutene," *Chem. Ind. Dev*, pp. 32–41 (1974).

It is generally known that n-paraffins with, for example, 4 to 7 carbon atoms can be converted to the corresponding isomeric paraffins by using suitable bifunctional (acid and metal) catalysts in the temperature range of from 100° to 250° C. Examples of this process are the numerous isomerization processes used in the petrochemical and mineral oil industries for increasing the octane number of light, paraffinic mineral oil fractions. Furthermore, it is known that, in contrast to this, olefins of the same number of carbon atoms cannot be converted to the corresponding isoolefins except under difficult conditions, for example at very high temperatures and with poor yield. The attempts hitherto described in the literature for the direct isomerization of the skeleton of e.g. n-butene to give isobutene or e.g. of n-pentene to give isoamylenes over catalysts arranged in a fixed bed are characterized by initially relatively low yields and selectivities, which can diminish and deteriorate further after a short period of operation, often after only a few hours. The deterioration in the yields and selectivities is generally attributed to the loss of actively effective catalyst surface or to the loss of active centers. In addition to this, high coking rates, formation of oligomers and cracking reactions are observed.

As is known, pentenes exist in six isomers. Conversions between the cis and trans 2-pentenes are known as geometric isomerization, whereas those between 1-pentene and the 2-pentenes are known variously as position isomerization, double-bond migration, or hydrogen-shift isomerization. These three isomers are not branched and are known collectively as normal or n-pentenes. Conversion of the n-pentenes to the isoamylenes, i.e., 2-methyl-1-butene, 2-methyl-2-butene or 3 methyl-1-butene, which are branched isomers collectively known as isoamylenes, is widely known as skeletal isomerization.

Also, isoamylenes or more specifically, the 2-methylbutenes have become more and more important recently as one of the main raw materials used in the production of tertiary amyl methyl ether (TAME), an environmentally-approved octane booster and source of oxygen in gasoline. However, processes for the skeletal isomerization of olefins, e.g., to produce isoamylenes, are relatively non-selective, inefficient, and short-lived because of the unsaturated nature of these compounds. On the other hand, positional and skeletal isomerization of paraffins and alkyl aromatics are fairly well established processes, in general utilizing catalysts typically comprising metallic components and acidic components, under substantial hydrogen pressure. Since paraffins and aromatics are relatively stable compounds, these processes are quite successful. The heavier the compounds, in fact, the less severe the operating requirements. Olefins, however, are relatively unstable compounds. Under hydrogen pressure, they are readily saturated to the paraffinic state if a metal component is present in the catalyst.

Furthermore, in the presence of acidity, olefins can polymerize, crack and/or transfer hydrogen. Extensive polymerization would result in poor isoolefin yields, and short operating cycles. Similarly, cracking would reduce yield. Hydrogen transfer would result in saturated and highly unsaturated compounds, the latter being the common precursors for gum and coke. Any theoretical one step process for producing skeletal isomers of, for example, n-pentenes, would have to be concerned with the unwanted production of olefin oligomers, saturates and cracked products.

Skeletal isomerization of olefins is known to be accomplished by contacting unbranched or lightly branched olefins with acidic catalysts at elevated temperatures. The process is generally applicable to the isomerization of olefins having from about 4 to about 12 carbon atoms, and is especially applicable to olefines having from about 4 to about 6 per molecule. The process may be used to form isobutene from normal butenes, methylpentenes and dimethylbutenes from normal hexenes, and so forth.

Thus, among the objects of this invention are improved catalysts for the skeletal isomerization of n-pentenes to form isoamylenes on pretreated zeolite catalysts.

Other objects and advantages of the invention will be apparent from the following description, including the drawing and the appended claims.

DISCLOSURE STATEMENT

Known skeletal isomerization catalysts include aluminas and halogenated aluminas, particularly F- or Cl-promoted aluminas. Supports employed in such catalysts are either alumina or predominantly alumina due mainly to the high acidity of alumina. See Choudhary, V. R., "Fluorine Promoted Catalysts: Activity and Surface Properties", *Ind. Eng. Chem., Prod. Res. Dev.*, 16(1), pp. 12–22 (1977) and U.S. Pat. Nos. 3,584,070 and 4,367,362. Numerous catalysts employ a metal or metal oxide in conjunction with a halide-treated metal oxide. For example, U.S. Pat. No. 4,410,753 discloses isomerization catalysts comprising $Bi_2O_3$ on fluorided alumina and U.S. Pat. No. 4,433,191 discloses skeletal isomerization catalysts comprising a Group VIII metal on halided alumina. Many of the catalysts including halide-treated components require periodic addition of halide materials to maintain catalyst activity; for example, see U.S. Pat. Nos. 3,558,734 and 3,730,958. An average yield for isoamylenes of 34 weight percent (within an observed range of 21 to 49 percent) is typically reported when using halided catalysts, based upon a review of various patents cited in this disclosure.

Various techniques have been employed to improve the effectiveness of materials such as alumina and silica as structural isomerization catalysts. Such catalysts are disclosed in the article of Otremba, M. and Taniewski, M. of "Double Bond Migration and Skeletal Isomerization of Olefins on Fluorinated Aluminas"; *React. Kinet. Catal. Lett.*, 15 (2) pp., 279–284 (1980). And, moreover: U.S. Pat. No. 3,558,733 discloses methods for activating alumina catalysts with steam; U.S. Pat. Nos. 4,038,337; 4,405,500 and 5,043,523 disclose catalysts prepared by controlled deposition of silica on alumina; U.S. Pat. Nos. 4,400,574; 4,404,416 and 4,404,417 disclose catalysts of fluorine or chlorine on alumina; and U.S. Pat. No. 4,587,375 discloses a steam-activated silicalite catalyst. In addition, various metal oxides have been used to improve the effectiveness of catalysts based upon alumina, silica or the like.

Zeolitic materials, especially in their hydrogen forms, are known to behave as strong acids. Due to their narrow yet regular pore size many are quite effective in catalyzing olefin polymerization. Unfortunately the pores are soon plugged due to deposition of polymeric materials and frequent catalyst regeneration is necessary to maintain activity.

U.S. Pat. Nos. 4,429,176; 4,522,929 and 4,594,146 disclose a zeolite of improved stability for use in acid-catalyzed reactions that is prepared by mildly presteaming the catalyst under controlled conditions of temperature, time, and steam partial pressure. The resulting catalyst retains nearly the same activity as that of a fresh unsteamed catalyst.

U.S. Pat. No. 4,663,492 discloses a feedstock of low molecular weight oxygenates such as methanol and/or dimethylether is contacted with a mildly presteamed or hydrothermally treated zeolite catalyst in a reaction zone to produce liquid hydrocarbons in the gasoline boiling range. The pretreated zeolite catalyst has an alpha-value (acid cracking activity) substantially the same as the alpha-value of fresh unsteamed catalyst and shows increased stability and resistance to aging under oxygenate conversion conditions of elevated temperature and pressure.

SUMMARY OF THE INVENTION

In accordance with the present invention, a catalyst composition for the skeletal isomerization of normal olefins comprises at least one zeolite catalyst. The present invention provides a method of isomerization with a pretreated zeolite catalyst.

This invention provides a method of selectively converting n-pentenes to 2-methylbutenes by a skeletal isomerization reaction wherein said reaction is carried out for 10 to 16 hours at a temperature of between 200° C. and 550° C., under a pressure of between 0.1 and 100 atmospheres and a space velocity of said n-pentenes of between 0.1 and 50 WHSV in the presence of a steam pretreated zeolite catalyst comprising a zeolite having a pore size of at least about 4.2 angstroms and less than 6.0 angstroms, and the pore size structure is characterized by intersecting 10-member ring and 8-member ring channels.

DETAILED DESCRIPTION OF THE INVENTION

Because of their unique pore structures, zeolites exhibit the so-called shape selectivity. In the isomerization of n-pentenes to isopentenes, oligomerization is the major competitive reaction. It has been postulated that a larger space is favorable for the oligomerization reaction because two olefin molecules are involved, therefore the oligomerization will be suppressed in a smaller pore structure. In his article [*Scientific American*, pgs. 112–118, April, 1992] J. M. Thomas has predicted that Theta-1 is better than ZSM-5 for the isomerization of n-butene. Both zeolites have 10-member ring channels and pore sizes of 4.4 to 5.6 A. In ZSM-5 the 10-member ring channels intersect, creating bigger cavities. However, in Theta-1, the channels do not intersect, and there are no extra cavities.

For the purpose of this application, a medium pore zeolite is one with a channel of 10 member ring (10-MR) and a channel dimension between 4.2 and 6.0. The preferred structures are those with 10-MR and 8-member ring (8-MR) intersecting channels, such as ferrierite. In Table I, below, there is a list of zeolites useful according to the present invention.

TABLE I

| ZEOLITES WITH 10 AND 8-MR INTERSECTED CHANNELS | | | |
|---|---|---|---|
| NAME | | CHANNELS | ISOTOPIC FRAMEWORK STRUCTURES |
| Dachiardite(DAC) | [010] | 10  3.4 × 5.3*<-> | ZSM-35, NU-23, |

TABLE I-continued

ZEOLITES WITH 10 AND 8-MR INTERSECTED CHANNELS

| NAME | | CHANNELS | | ISOTOPIC FRAMEWORK STRUCTURES |
|---|---|---|---|---|
| | [001] | 8 | 3.7 × 4.8* | FU-9, ISI-6 |
| Epistilbite(EPI) | [100] | 10 | 3.4 × 5.6*<-> | |
| | [001] | 8 | 3.7 × 5.2* | |
| Ferrierite(FER) | [001] | 10 | 4.2 × 5.4*<-> | |
| | [010] | 8 | 3.5 × 4.8* | |
| Heulandite(HEU) | [100] | 8 | 2.6 × 4.7*<-> | |
| | [001] | 10 | 3.0 × 7.6*+ | |
| Stilbite(STI) | [100] | 10 | 4.9 × 6.1 <-> | |
| | [101] | 8 | 2.7 × 5.6* | |

<-> interconnecting channels
Data obtained from "Atlas of Zeolite Structure Types," by W. M. Meier and D. H. Olson, Butterworths, 1987, 2nd Edition.

When the zeolites are prepared in the presence of alkali or organic cations they are initially catalytically inactive, possibly because the intracrystalline free space is occupied by cations from the forming solution. They may be activated by heating in an inert atmosphere at 550° C. for one hour, for example, followed by exchange with ammonium salts followed by calcination at 550° C. in air. The presence of organic cations in the forming solution may not be absolutely essential to the formation of the zeolite but these cations can favor the formation of the desired crystal structures.

In commercial practice, the zeolite crystallites would be bound together within a matrix comprising alumina, silica, silica-alumina, alumina-aluminum phosphate, clay or admixtures thereof. Normally, the finished catalyst would contain at least 10 up to about 85 weight percent of such a binder or matrix. The alumina which is used for the matrix material for the catalyst system of the present invention can be any suitable grade of crystalline or amorphous alumina which is substantially inert.

Matrix materials which can be used as binders can be prepared in the same manner as that employed for the preparation of amorphous catalysts. A catalyst can be prepared by adding the zeolite component to a slurry of the binder, extruding or spray drying, washing the product and drying. The catalyst is then calcined to confer the required physical strength. The matrix can consist of colloidal alumina (boehmite) or colloidal silica, allowing the matrix properties to vary over a wide range from catalytically inert to active. The activity, thermal stability, surface area and pore distribution of the matrix can be controlled by varying the amounts and particle size distributions of the respective colloids. Further guidance for the preparation of zeolite catalysts containing high porosity matrixes such as silica-alumina can be found in the section by Magee and Blazek on "Zeolite Cracking Catalysts" in ACS Monograph 171, *Zeolite Chemistry and Catalysts* (J. Rabo, Ed.; Am. Chem. Soc., Wash, D.C. 1976).

The amount of binder or other matrix material relative to zeolite in the composite will determine, to a certain extent, the physical strength of the final catalyst, especially its attrition resistance and crushing strength. The mechanical properties of the catalyst can therefore be modified by appropriate choice of matrix/zeolite ratio, with greater amounts of matrix generally conferring better mechanical properties. On the other hand, larger amounts of matrix mean that less of the zeolite with its desired, attendant properties will be available to participate in the eventual reaction. A balance will therefore be struck, in most cases, between activity and mechanical properties. Normally, the amount of matrix material will not exceed 50 percent by weight of the composite and in most cases it will not exceed 40 percent by weight and may be lower, e.g. 25 percent by weight or even 15 percent by weight.

The zeolite may conveniently be composited with the matrix materials by forming an aqueous slurry of the zeolite with the matrix material, spray drying the slurry to form spheres and then calcining. Alternatively, extrudates or pellets can be formed from matrix and zeolite mixtures. If one of the zeolites in the zeolite combination is capable of being produced by treatment of a clay, the zeolite may be composited with the clay slurry and the slurry spray dried to form solid zeolite/clay spheres which are then calcined to confer the desired strength. The clay in the composite may then be converted to the zeolite in the conventional way, e.g. by treatment with sodium hydroxide and heating, followed by ion-exchange, if desired. The mixing and homogenizing steps which may be used in the preparation of the zeolite-matrix mixtures are conventional and need not be described; the spray drying may also be carried out in the conventional manner.

According to the present invention, this is provided as a mild steam treatment of select, medium pore (10-member ring) zeolites bound in an alumina matrix which moderates the resulting initial catalytic activity and improves the selectivity in the skeletal isomerization of n-pentenes to isoamylenes. This treatment should not be confused with the typical steaming of a zeolite crystal (in the absence of any binder matrix) that results in the extraction of aluminum ions from the zeolite to produce a more active and thermally stable (i.e. higher Si to Al ratio) zeolite.

Figure 1:
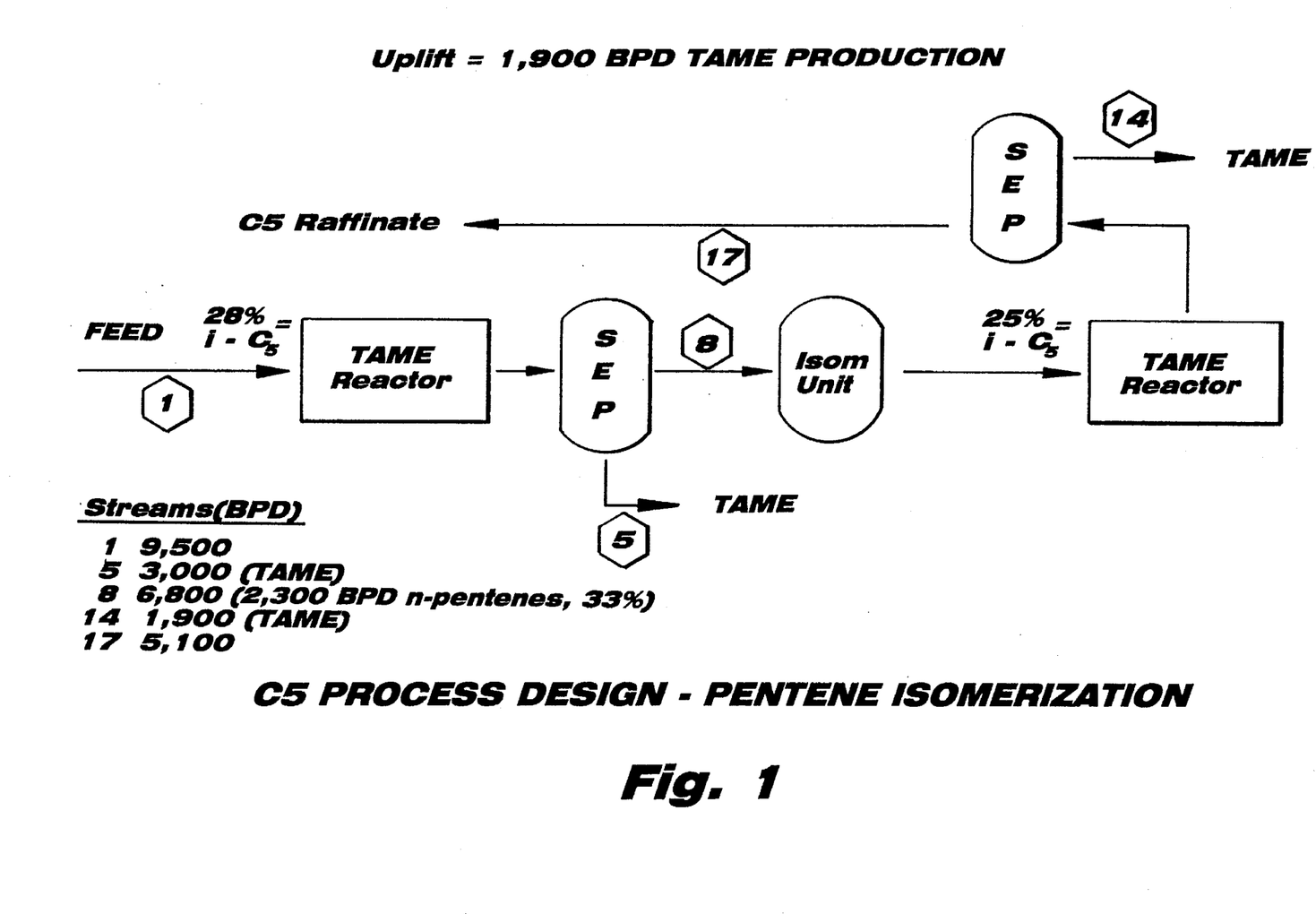
FIG. 1 is a flow diagram illustrating the present method of skeletal isomerization.

Referring to the process flow diagram of FIG. 1, the skeletal isomerization of the n-pentenes present in the $C_5$ raffinate stream from a 3000 bpd TAME unit generates additional 2-methylbutenes (isoamylenes) sufficient to provide a 1900 bpd uplift in TAME production. A zeolite based catalyst has been identified as quite active and very selective in catalyzing the skeletal isomerization of n-pentenes to isoamylenes. In particular, an alumina-bound ferrierite zeolite catalyst was found to be quite active and selective with lifetimes of 24 to 48 plus hours.

Figure 2:
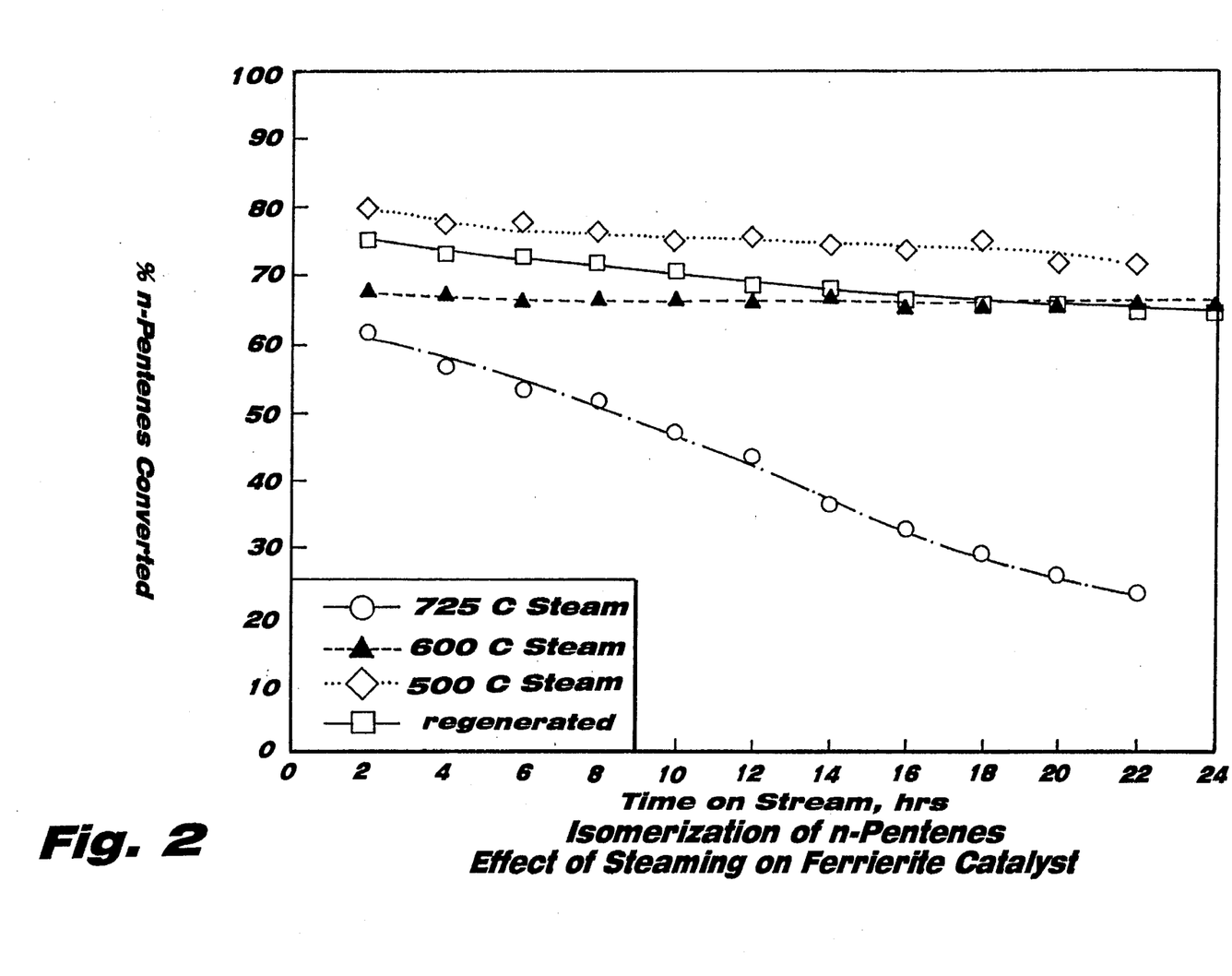
FIG. 2 is a graph illustrating the effect of the steaming temperature on ferrierite catalyst in the conversion of n-pentenes in the present method of skeletal isomerization.
Figure 3:
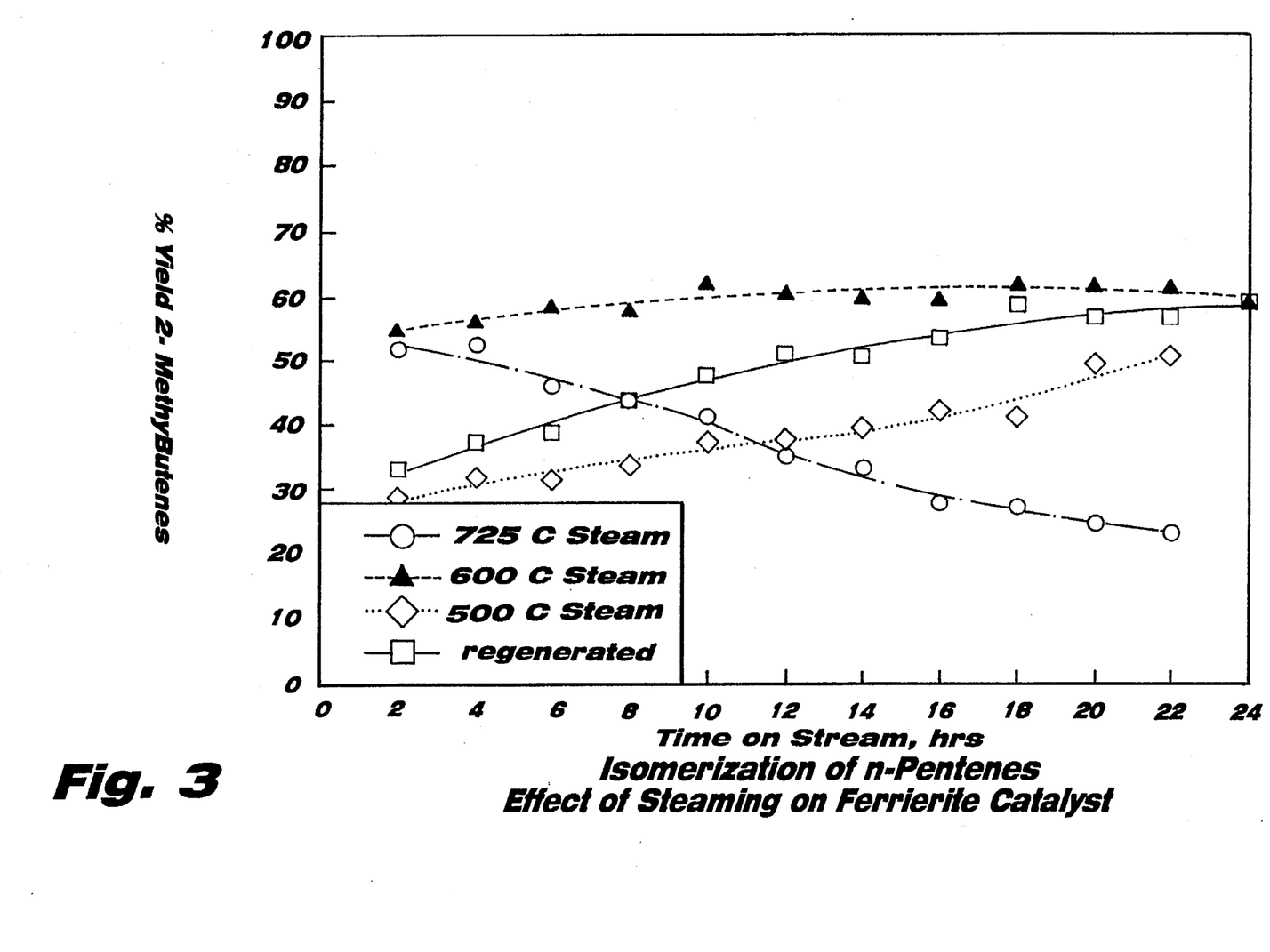
FIG. 3 is a graph illustrating the effect of the steaming temperature on ferrierite catalyst in the yield of 2-methylbutenes from the conversion of n-pentenes.

The problem overcome by the present invention is that the unmodified ferrierite in alumina catalyst exhibits an initial activity "edge" (lasting approximately 12 to 16 hrs, see FIG. 2) resulting in excessively high n-pentene conversion with low selectivity/yield of 2-methylbutenes (see FIG. 3). The "edge" is still present, even after repeated catalyst regenerations (by controlled air burn of coke on catalyst), and the "edge" accounts for 25% or more of the run time. The initial "edge" in catalytic activity can be suppressed by steaming the catalyst (a H-ferrierite in an alumina binder) at the preferred temperature of about 600° C.

A comparison of various steam pretreatments at different temperatures is given below in Tables I, II and III and in FIGS. 2 and 3. It is obvious that the steam treatment at about 600° C. is preferred, is reproducible and appears quite stable for long term activity [(Run (5) vs repeated treatment in Run (9)]. Run (10) (see FIG. 4) shows that 600° C. steaming of a fresh H-ferrierite catalyst results in a run length of approximately 38 hrs before the catalyst begins to deactivate. A slight increase in Run Temperature can counteract the effects of catalyst deactivation and extend the run length.

The run results provided below in Tables I, II and III (i.e. conversion, selectivity and yield) were obtained at 2, 4 and 12 hrs-on-stream respectively unless noted otherwise. Results at 2 and 4 hrs relate to initial activity. Results at 12 hrs approximate the run average over 24 hrs. The feed to the skeletal isomerization reactor consisted of a mixture of $C_5$ components containing 35.83% n-pentenes, 8.21% isoamylenes and 55.96% pentanes.

TABLE I

Catalyst Evaluation For (C5) Skeletal Isomerization

| | RUN | | | |
|---|---|---|---|---|
| | 1<br>Ferrierite<br>(Fresh) | 2<br>Regenerated<br>Ferrierite | 3<br>Regenerated<br>600° C. Steamed<br>Ferrierite | 4<br>Regenerated<br>725° C. Steamed<br>Ferrierite |
| Conversion<br>n-pentenes | 77,75,72 | 76,74,68 | 68,68,66 | 62,56,41 |
| Selectivity to<br>2-methylbutenes | 35,38,51 | 42,50,75 | 76,74,83 | 84,94,85 |
| Yield of<br>2-methylbutenes | 27,29,37 | 32,37,51 | 52,51,55 | 52,53,36 |
| Equilibrium<br>Approach<br>isoC5=/all C5= | .68,.67<br>.67 | .69,.69<br>.70 | .70,.69<br>.69 | .66,.63,<br>.49 |

*Catalyst evaluations at 350° C., 15 psig, at a 7.30 hr$^{-1}$ WHSV using a mixture of C5 model compounds as feed.

TABLE II

Catalyst Evaluation* For (C5) Skeletal Isomerization

| | RUN | | | |
|---|---|---|---|---|
| | 5<br>Ferrierite<br>(Fresh) | 6<br>Regenerated<br>400° C. Steamed<br>Ferrierite | 7<br>Regenerated<br>500° C. Steamed<br>Ferrierite | 8<br>Regenerated<br>600° C. Steamed<br>Ferrierite |
| Conversion<br>n-pentenes | 76,73,71 | 81,77,76 | 80,78,75 | 67,68,66 |
| Selectivity to<br>2-methylbutenes | 47,55,67 | 29,43,47 | 35,40,51 | 85,80,86 |
| Yield of<br>2-methylbutenes | 35,41,47 | 23,33,36 | 28,31,38 | 57,54,57 |
| Equilibrium<br>Approach<br>isoC5=/all C5= | .69,.69<br>.69 | .68,.69<br>.69 | .69,.69<br>.69 | .70,.70,<br>.69 |

*Catalyst evaluations at 350° C., 15 psig, at a 8.00 hr$^{-1}$ WHSV using a mixture of C5 model compounds as feed.

TABLE III

Catalyst Evaluation* For (C5) Skeletal Isomerization

| | RUN | |
|---|---|---|
| | 9<br>Regenerated<br>2nd 600° C. Steaming<br>of Ferrierite<br>(Results at 2,4,12 hrs) | 10<br>Fresh Ferrierite<br>600° C. Steamed<br>(Results at<br>2,12,24,36 hrs) |
| Conversion<br>n-pentenes | 66,63,63 | 68,66,65,60 |
| Selectivity to<br>2-methylbutenes | 92,100,100 | 81,92,92,97 |
| Yield of<br>2-methylbutenes | 61,63,63 | 55,61,60,58 |
| Equilibrium<br>Approach<br>isoC5=/all C5= | .70,.70<br>.70 | .70,.70,.69,.66 |

*Catalyst evaluations at 350° C., 15 psig, at a 8.00 hr$^{-1}$ WHSV using a mixture of C5 model compounds as feed.

Spent catalysts can be regenerated by heating in a similar oxygen-containing gas, such as air or air-nitrogen mixtures, at temperatures ranging from about 200° C. to about 700° C. This process is significantly simpler than that required for halided metal oxide catalysts, in which a separate step of replacing the halide component must be employed.

The skeletal isomerization processes of this invention are carried out by contacting the feed with the catalyst, using any suitable contacting techniques, at temperatures at which skeletal isomerization of the feed of olefins occurs. The feed is preferably maintained in the vapor phase during contacting. The reactor temperature is preferably in the range of about 250° to about 550° C., more preferably about 250° to about 500° C. The weight hourly space velocity (WHSV) is not narrowly critical but will generally be within the range of about 0.1 to about 50 $hr^{-1}$, preferably from about 1 to about 40 $hr^{-1}$. Any convenient pressure can be used, with the lowest practical pressure preferred in order to minimize side reactions such as polymerization. Preferred pressures are within the range of about 0.1 to about 100 atmospheres, more preferably about 0.5 to about 4 atmospheres.

The isomerization feedstock contains at least one alkene. Alkenes having 7 or more carbon atoms are generally more likely to crack into light gases than to undergo skeletal isomerization. The alkenes may have terminal or internal double bonds. Pentene feed-stocks may contain 1-pentene, 2-pentenes or mixtures thereof. Examples of other normal alkenes which are useful feedstocks are 1-and 2-butenes; 1-, 2- and 3-hexenes; 1-, 2-, and 3-heptenes; and 1-, 2-, 3-, and 4-octenes.

Particular feedstocks contemplated for use in the present process are fractions containing pentenes, e.g., n-pentenes.. The 2-methylbutenes present in such fractions are commonly converted by catalytic reaction with methanol to produce tertiary-amyl methyl ether ("TAME"). TAME is separated by distillation, leaving a residual $C_5$ cut. Alternatively, isoamylenes present in such fractions may also be oligomerized to produce oligomers which are then separated, again leaving a residual $C_5$ cut. In either TAME production or oligomerization, a mixture of n-pentenes along with smaller amounts of isopentenes remains in the residual material. It is desirable to produce additional isopentenes from the residual material and return the isopentene for further conversion by the reactions mentioned above.

The isomerization feed stream can contain inert gaseous diluents (e.g. paraffins, $N_2$, steam, etc.). The diluent may be present in any desired proportion, e.g., up to about 80 weight percent of the feed stream. Hydrogen can be present in the feed stream in addition to such diluents, and with or without steam can have beneficial effects on the product yield and selectivity as well as catalyst life times.

Selection of isomerization conditions is dependent on the olefins to be isomerized. In general, lower temperatures are used for feeds containing larger olefin molecules. Depending on the specific skeletal isomerization catalysts chosen to carry out the steps of the invention, any suitable reaction technique can be utilized, such as fixed bed reaction, fluidized bed reaction, liquid phase batch and continuous operations, and the like. Conventional methods can be used to separate the materials present in the reaction effluent, including fractionation, crystallization, adsorption, and the like. Fractionation is generally preferred. Saturated materials which accumulate in the system can easily be removed by suitable techniques well known in the art.

In one aspect of the process according to the present invention, the conversion of n-alkenes into isoalkenes, preferably pentenes into isoamylenes, almost up to the establishment of thermodynamic equilibrium is achieved. This equilibrium, between 200° to 500° C., is about 90 to 75 percent by weight in the case in which the pure system of the n-pentenes and isoamylenes is considered. This equilibrium may not be achieved in the case of a single contact of the mixture to be employed according to the present invention with the catalyst to be employed during the present process. However, in a particular variant of the process, the product stream leaving the catalyst bed can be divided up, and only one part is directly conveyed to the working-up process, while the other part is again conducted over the catalyst bed. This division of the product stream for recycling can vary within wide limits, for example between the proportions of 1:9 to 9:1 of worked-up or recycled material. In this process, a high recycling rate implies a smaller throughput, relative to a constant catalyst charge and constant remaining reaction conditions, but brings a desired shift of the spectrum of components in favor of the isoalkene, e.g., of the isoamylenes, almost to the thermodynamic equilibrium. On the other hand, a lower recycling rate implies a higher throughput but a poorer approach to the thermodynamic equilibrium. A decision concerning the amount of the recycling rate depends, other process parameters being constant, above all on the composition of the starting hydrocarbon mixture which is available. However, with the catalysts according to the present invention, the process can, in general, be operated without a high recycling rate. This can be optimized by simple preliminary experiments.

The process also can be carried out under the following conditions:

1. The reactor temperature is between 200° and 550° C., the pressure is between 0.1 and 100 atmospheres, and the space velocity of n-pentenes (WHSV) is between 0.1 and 50. The preferable reactor conditions are 250° to 500° C., 0.5 to 4 atm, and 1 to 40 WHSV of n-pentenes.
2. Diluents, such as steam, nitrogen, paraffins etc., can be used in the feed to improve the selectivity and yield.
3. The feeds can be 1-pentene, mixed n-pentenes, and $C_5$-raffinates depleted in isopentenes. The process also can be applied to the other n-olefins, such as n-butenes and n-hexenes.

According to the present invention, a preferred embodiment of the invention is directed to an integrated process for skeletal isomerization of normal pentenes to produce isoamylenes, which is then used in the production of tertiary-amyl methyl ether (TAME). Streams of a mixed pentene feedstock and methanol are reacted in a TAME synthesis reactor, the methanol reacting with the 2-methylbutenes in the mixed feedstock to form TAME which is then taken off via an exit line. The TAME synthesis reactor acts as a $C_5$ separation unit, since the methanol reacts selectively with 2-methylbutenes. Other mixed olefin streams could be treated in the same manner. Other alcohol streams could be employed in a similar manner; e.g., reacting ethanol with mixed pentenes to form tertiary-amyl ethyl ether (TAEE). The alcohol stream can contain at least one alkanol having from 1 to about 5 carbon atoms. Depending upon whether streams containing substantially single alcohols or mixtures thereof are employed, the corresponding alkyl tertiary-alkyl ether or mixtures containing various groups can be produced.

The product $C_5$ raffinate stream is fed to a skeletal isomerization unit wherein a catalyst of the present invention is employed to isomerize normal pentenes to isoamylenes for use as feed to the TAME reactor. Hydrogen or steam can be introduced into isomerization section to improve reactor performance. Saturated species which are unsuitable for isomerization can be separated and purged from the raffinate via an exit line, or as part of the byproducts ($C_1$–$C_4$) gases and polygas) which are separated from the isomerization section via other exit lines.

Such an integrated process permits a mixed feed stream of pentenes (or other alkanes and/or alkenes) to be used most effectively in the production of TAME (or other alkyl tertiary-alkyl ethers) via the skeletal isomerization of alkenes and recycle to the TAME reactor. The skeletal isomerization processes and catalysts of the present invention are of course useful in processing feed streams containing normal alkenes from a variety of sources.

EXAMPLES

The present invention is further illustrated by reference to the following examples.

EXAMPLE I

Preparation of Catalysts

In this example, a commercially available ferrierite catalyst, TSZ-720* was used; the catalyst contained 80% ferrierite and 20% alumina binder. The chemical composition of ferrierite was 84.7% $SiO_2$, 8.1% $Al_2O_3$, 1.45% $Na_2O$, and 5.6% $K_2O$; it was in [$K^+$/$Na^+$]form. The catalyst was ion-exchanged twice with $NH_4NO_3$ to form [$NH_4^+$]-ferrierite. About 5 grams of catalyst was mixed with 5 grams of $NH_4NO_3$ and 15 milliliters of water; the mixture was stirred at 90° C. for two hours. The exchanged catalyst was washed, dried, and calcined at 550° C. to form [$H^+$]-ferrierite. The catalyst was subjected to a steam treatment prior to use at a temperature of about 600° C., a pressure of 1.0 atmosphere with an atmosphere of 100% steam for a period of 16 hrs. The composition of the finished catalyst had 0.12% K and <0.05% Na. Additional samples of catalysts were prepared by subjecting the ferrierite catalyst to a steam pretreatment at 400°, 500° or 725° C.

*TSZ-720 - Catalyst (zeolite-based) by TOSOH USA INC., of Atlanta, Ga.
The catalysts also could be prepared by the following ways:

1. The zeolites should have a pore size approximately that of the kinetic diameter of isopentene. The favorable zeolites are those with 10-member ring (MR) and 8-MR intersecting channels. In Table I, above, is a list of 10-MR zeolites provided, which can be used.
2. The mole ratio of Si/Al is between about 4 and about 1000.
3. The pore structure of zeolites can be modified by known methods, such as steam calcination, impregnation, and ion-exchange to enhance the activity and shape selectivity.
4. The zeolites are bound together using alumina, silica, silica-alumina, alumina-aluminum phosphate, clay or a combination of them. The weight percent of binder is between 0–99%.
5. The catalyst is subjected to a steam treatment prior to use under the temperature ranges of about 300° to 700° C., preferably 600° C., the pressure ranges from 0.5 to 4.0 atmosphere with an atmosphere of 5 to 100% steam for a period of 2–25 hrs.

EXAMPLE II

Testing of Catalysts

The catalyst of Example I was tested for its activity in the isomerization of n-pentenes to 2-methylbutenes. The reaction conditions were: 350° C., 15.0 psig and a WHSV of 8.0 $hr^{-1}$ based on total feed (3.52 $hr^{-1}$ based on olefin content). The feed to the skeletal isomerization reactor consisted of a mixture of $C_5$ components containing 35.83% n-pentenes, 8.21% isoamylenes and 55.96% pentanes.

Referring to FIG. 3, results are illustrated there of 2-methylbutene yield over 22 hr. For the untreated regenerated catalyst, the percent yield of 2-methylbutenes after 2 hours on stream was relatively low at about 30%. The yield gradually increased up to about 57% over 22 hours. For the 600° C. steamed pretreated catalyst, the 2-methylbutene yield started at 57% and increased sightly to 60% over 22 hrs.

Figure 4:
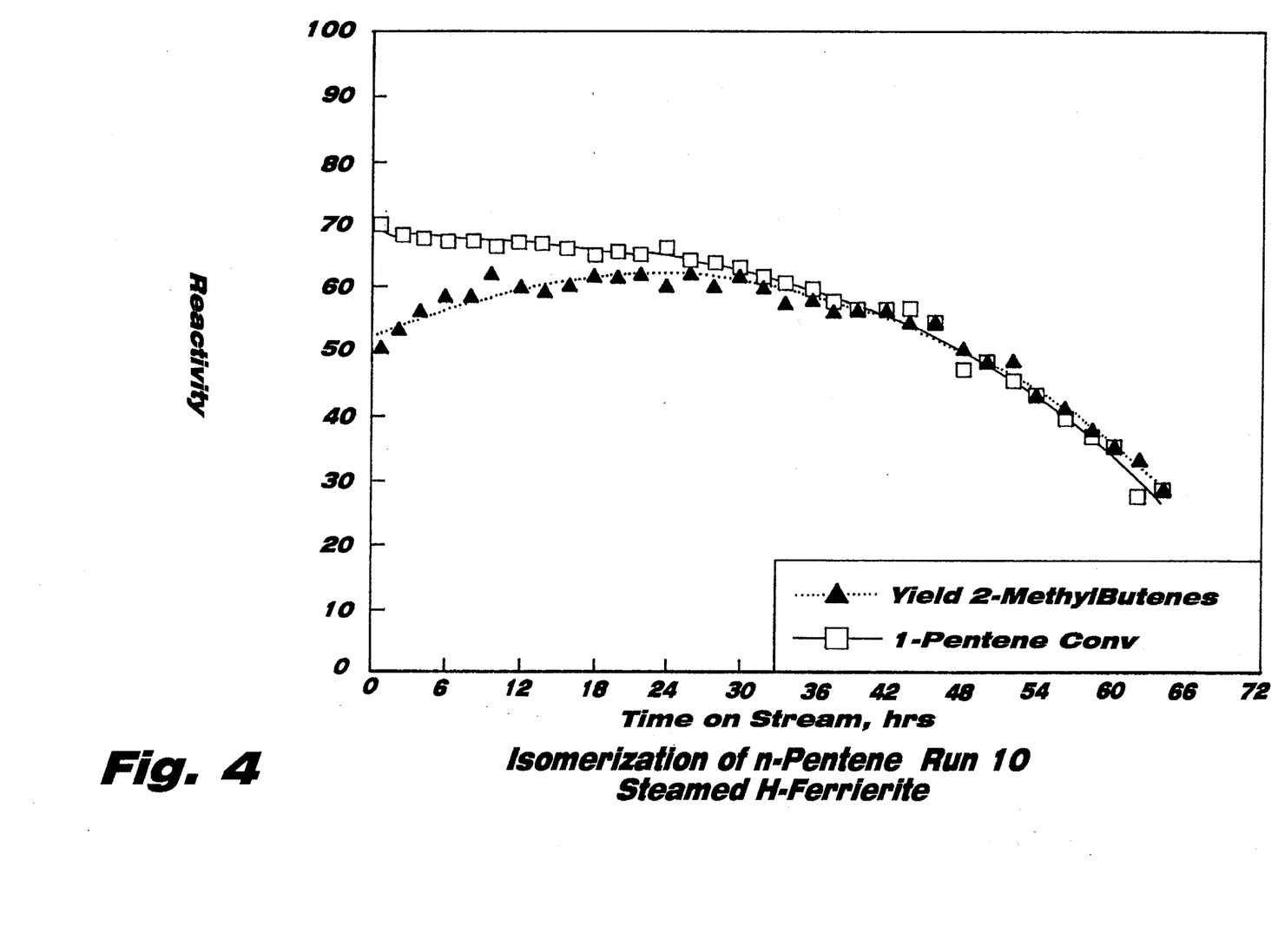
FIG. 4 is a graph illustrating the reactivity of the steamed ferrierite zeolite as to both the yield of 2-methylbutenes and conversion of 1-pentenes from the isomerization of n-pentenes.

The data of FIG. 4 shows that the 600° C. steamed pretreatment of the ferrierite catalyst can maintain its selective activity for a period of at least 36 hrs.

We claim:

1. A process for the skeletal isomerization of an n-olefin of from 4 to 12 carbon atoms to provide a branched olefin product which comprises contacting the n-olefin under skeletal isomerization conditions with, as skeletal isomerization catalyst, a steam pretreated, alumina matrix-bound zeolite catalyst, said zeolite having a pore size of at least about 4.2 angstroms and less than 6.0 angstroms and a pore structure characterized by intersecting 10-member ring and 8-member ring channels.

2. The process of claim 1 wherein the skeletal isomerization conditions include a temperature of between about 200° C. and 550° C., a pressure of between about 0.1 and about 100 atmospheres and a space velocity of n-olefin of between 0.1 and 50 weight hourly space velocity.

3. The process of claim 1 wherein the n-olefin is an n-butene.

4. The process of claim 1 wherein the zeolite is an aluminosilicate or an isomorphously substituted T-zeolite in which T is B, Ga or Fe.

5. The process of claim 1 wherein the skeletal isomerization conditions include a temperature of between about 250° C. and 500° C., a pressure of between about 0.5 to 4.0 atmospheres and a space velocity of n-olefin of between about 1.0 and 40 weight hourly space velocity.

6. The process of claim 1 wherein the zeolite is selected from the group consisting of dachiadite, epistilbite, ferrierite, heulandite, stilbite and any combination thereof.

\* \* \* \* \*